US00RE41741E

(19) United States
(12) Reissued Patent
Dinsmore

(10) Patent Number: US RE41,741 E
(45) Date of Reissued Patent: Sep. 21, 2010

(54) OPTICALLY DRIVEN THERAPEUTIC RADIATION SOURCE HAVING A SPIRAL SHAPED THERMIONIC CATHODE

(75) Inventor: Mark Dinsmore, Sudbury, MA (US)

(73) Assignee: Carl Zeiss AG, Oberkochen (DE)

(21) Appl. No.: 10/790,636

(22) Filed: Mar. 1, 2004

(Under 37 CFR 1.47)

Related U.S. Patent Documents

Reissue of:
(64) Patent No.: 6,493,419
Issued: Dec. 10, 2002
Appl. No.: 09/884,229
Filed: Jun. 19, 2001

(51) Int. Cl.
*A61N 5/10* (2006.01)

(52) U.S. Cl. ..... 378/65; 378/121; 378/136
(58) Field of Classification Search ..... 378/64, 378/65, 119, 121, 136, 138, 143
See application file for complete search history.

(56) References Cited

U.S. PATENT DOCUMENTS

| | | | | | |
|---|---|---|---|---|---|
| 4,878,866 | A | * | 11/1989 | Mori et al. | 445/36 |
| 5,090,043 | A | | 2/1992 | Parker et al. | 378/121 |
| 5,153,900 | A | | 10/1992 | Nomikos et al. | 378/65 |
| RE34,421 | E | | 10/1993 | Parker et al. | 378/121 |
| 5,369,679 | A | | 11/1994 | Sliski et al. | 378/65 |
| 5,422,926 | A | | 6/1995 | Smith et al. | 378/121 |
| 5,428,658 | A | * | 6/1995 | Oettinger et al. | 378/119 |
| 5,504,799 | A | * | 4/1996 | Suzuki | 378/136 |
| 5,621,780 | A | | 4/1997 | Smith et al. | 378/65 |
| 5,621,781 | A | | 4/1997 | Blake et al. | 378/138 |
| 6,319,188 | B1 | | 11/2001 | Lovoi | 600/3 |
| 6,320,935 | B1 | * | 11/2001 | Shinar et al. | 378/119 |
| 6,324,257 | B1 | | 11/2001 | Halavee | 378/121 |
| 2006/0233307 | A1 | | 10/2006 | Dinsmore | |

FOREIGN PATENT DOCUMENTS

| | | |
|---|---|---|
| JP | 3-285239 | 12/1991 |
| WO | WO 93/04735 | 3/1993 |
| WO | WO 95/20241 | 7/1995 |
| WO | WO 01/47596 | 7/2001 |

* cited by examiner

*Primary Examiner*—Courtney Thomas
(74) *Attorney, Agent, or Firm*—John M. Garvey; Matthew L. Fenselau; Foley & Lardner, LLP

(57) ABSTRACT

A therapeutic radiation source includes a spiral-shaped, laser-heated thermionic cathode. A fiber optic cable directs a beam of radiation, having a power level sufficient to heat at least a portion of the electron-emissive surface to an electron emitting temperature, from a laser source onto the cathode. The cathode generates an electron beam along a beam path by thermionic emission, and strikes a target positioned in its beam path. The target includes radiation emissive material that emits therapeutic radiation in response to incident accelerated electrons from the electron beam. The spiral-shaped conductive element has a plurality of spaced apart turns, and is disposed in a vacuum. An interstitial spacing is defined between adjacent turns, so that heat transfer across the spacing between each adjacent turn is essentially eliminated, thereby substantially reducing heat loss in the cathode caused by thermal conduction.

30 Claims, 4 Drawing Sheets

OPTICALLY DRIVEN THERAPEUTIC RADIATION SOURCE HAVING A SPIRAL SHAPED THERMIONIC CATHODE

Matter enclosed in heavy brackets [ ] appears in the original patent but forms no part of this reissue specification; matter printed in italics indicates the additions made by reissue.

CROSS-REFERENCE TO RELATED APPLICATIONS

Not Applicable

STATEMENT REGARDING FEDERALLY SPONSORED RESEARCH

Not Applicable

REFERENCE TO MICROFICHE APPENDIX

Not Applicable

FIELD OF THE INVENTION

The present invention relates to therapeutic radiation sources, and in particular to miniaturized, highly efficient, optically-driven therapeutic radiation sources.

BACKGROUND OF THE INVENTION

In the field of medicine, radiation may be used for diagnostic, therapeutic and palliative purposes. For example, the therapeutic use of radiation such as x-rays and y-rays may involve eradicating malignant cells. Conventional radiation treatment systems used for medical treatment, such as linear accelerators that produce high-energy x-rays, utilize a remote radiation source external to the targeted tissue. A beam of radiation is directed at the target area, for example a tumor inside the body of a patient. The x-rays penetrate the patient's body tissue and deliver radiation to the cancer cells, usually seated deep inside the body. This type of treatment is referred to as teletherapy because the radiation source is located at some distance from the target. This treatment suffers from the disadvantage that tissue disposed between the radiation source and the target is exposed to radiation. To reach the cancer cells, the x-rays from an external radiation source must usually penetrate through normal surrounding tissues. Non-cancerous tissues and organs are therefore also damaged by the penetrating x-ray radiation.

An alternative treatment system utilizing a point source of radiation is disclosed in U.S. Pat. No. 5,153,900 issued to Nomikos et al., U.S. Pat. No. 5,369,679 to Sliski et al., U.S. Pat. No. 5,422,926 to Smith et. al., and U.S. Pat. No. 5,428,658 to Oettinger et al., all owned by the assignee of the present application, all of which are hereby incorporated by reference. This system includes a miniaturized, insertable probe capable of producing low power x-ray radiation while positioned within or in proximity to a predetermined region to be irradiated. The probe may be fully or partially implanted into, or surface-mounted onto a desired area within a treatment region of a patient. X-rays are emitted from a nominal, or effective "point" source located within or adjacent to the desired region to be irradiated, so that a desired region is irradiated, while irradiation of other regions are minimized. This type of treatment is referred to as brachytherapy, a word derived from the ancient Greek word for close ("brachy"), because the source is located close to or in some cases within the area receiving treatment.

Brachytherapy offers a significant advantage over teletherapy, because the radiation is applied primarily to treat a predefined tissue volume, without significantly affecting the tissue adjacent to the treated volume. The term brachytherapy is commonly used to describe the use of radioactive isotopes which can be placed directly within or adjacent the target tissue to be treated. Handling and disposing of such radioisotopes, however, may impose considerable hazards to both the handling personnel and the environment. X-ray brachytherapy offers the advantages of brachytherapy, while avoiding the use of radioisotopes.

X-ray brachytherapy treatment generally involves positioning the insertable probe into or adjacent to the tumor or the site where the tumor or a portion of the tumor was removed to treat the tissue adjacent the site with a local boost of radiation. Radiation probes of the type generally disclosed in U.S. Pat. No. 5,153,900 typically include a housing, and a hollow, tubular probe or catheter extending from the housing along an axis and having a target assembly at its distal end. The probe typically encloses an electron source having a thermionic cathode or a photocathode. The electron source also typically includes an accelerating means for establishing an acceleration potential difference between the electron source and the target. The target emits radiation in response to incident electrons from the electron source.

In conventionally heated thermionic cathodes, a filament is resistively heated with a current. This in turn heats the cathode so that electrons are generated by thermionic emission. In a typical conventional x-ray machine, for example, the cathode assembly may consist of a thoriated tungsten coil approximately 2 mm in diameter and 1 to 2 cm in length which, when resistively heated with a current of 4 A or higher, thermionically emits electrons. Thermionic cathodes must be stable against temperature rise under operation, since they may be subject to several thousand degrees centigrade. In a photocathode, a photoemissive substance is irradiated by a LED or a laser source. Typically, a flexible fiber optical cable couples light from the LED or laser source to the photocathode. The laser beam shining down the fiber optic cable activates the photocathode which generates free electrons by the photoelectric effect. Photocathodes may be subjected to several hundred degrees centigrade.

In order to prevent probe failure, it is important that the electron source be heated as efficiently as possible, namely that the electron source reach as high a temperature as possible using as little power as possible. In conventional x-ray tubes, for example, thermal vaporization of the cathode filament is frequently responsible for tube failure. Also, the anode heated to a high temperature can cause degradation of the radiation output. During relatively long exposures from an x-ray source, e.g. during exposures lasting from about 1 to about 3 seconds, the anode temperature may rise sufficiently to cause it to glow brightly, accompanied by localized surface melting and pitting which degrades the radiation output.

While a photocathode avoids such problems, there are difficulties inherent in fabricating the photocathode, because photocathode fabrication should preferably be done in a vacuum. A photocathode must have a sufficient quantum efficiency, where quantum efficiency relates to the number of electrons generated per incident light quantum. The degree of efficiency must be balanced to the intensity of available incident light. For practical substances, with reasonable quantum efficiencies above $10^{-3}$, the fabrication of the photocathode should be performed in a vacuum. U.S. Pat. No. 5,428,658, owned by the assignee of the present application and hereby incorporated by reference, discloses an example of such vacuum fabrication.

It is possible to further increase the efficiency of, and reduce the power requirements of, miniaturized therapeutic radiation sources as discussed above, by using a laser rather than an ohmic current, to heat the thermionic cathode. U.S. patent application Ser. No. (identified by Attorney Docket Nos. PHLL-155 and hereby incorporated by reference) (hereinafter the "PHLL-155" application) discloses a miniature therapeutic radiation source that uses a reduced-power, increased efficiency electron source. The electron source disclosed in the PHLL-155 application has a laser-heated thermionic cathode,.which generates electrons with minimal heat loss, and which does not require a vacuum-fabricated photocathode. The electron source includes a thermionic cathode having an electron emissive surface. The PHLL-155 application discloses using laser energy to heat the electron emissive surface of the thermionic cathode, instead of resistively heating the electron emissive surface of the thermionic cathode. In this way, electrons can be produced in a quantity sufficient to form an electron current necessary for generating therapeutic radiation at the target, while significantly reducing the requisite power requirements for the radiation source.

It is desirable that the surfaces of the thermionic cathodes be heated to as high a temperature as possible, and as rapidly as possible, i.e. that the surfaces be heated as efficiently as possible. Therefore, one way of reducing the power requirements for a therapeutic radiation source, such as the source disclosed in the PHLL-155 application, is to minimize heat loss by the thermionic cathode. Heat loss by laser-heated thermionic cathodes may include 1) heat lost by thermal conduction; and 2) heat loss caused by the portion of incident laser radiation that remains unabsorbed; and 3) heat loss by thermal radiation. One of the features disclosed in the PHLL-155 application are reflector elements. These reflector elements can reflect back to the thermionic cathode incident laser radiation that remained unabsorbed by the electron emissive surface of the thermionic cathode, thereby minimizing heat loss due to unabsorbed incident laser radiation. These reflector elements cannot reduce, however, heat loss that is caused by thermal conduction in the thermionic cathode.

It is an object of this invention to reduce heat loss that is caused by thermal conduction in a laser heated thermionic cathode, thereby further increasing the efficiency of a laser-driven therapeutic radiation source and reducing the power requirements therefor. It is another object of this invention to provide a thermionic cathode for use in a therapeutic radiation source, where the thermionic cathode is shaped and configured so as to reduce heat loss caused by thermal conduction within the cathode.

SUMMARY OF THE INVENTION

The invention relates to a highly efficient, miniaturized source of therapeutic radiation, such as x-rays. The therapeutic radiation source has an optically-driven thermionic cathode that is spiral-shaped. In this way, heat loss due to thermal conduction within the thermionic cathode is minimized.

A fiber optic cable directs a beam of radiation, having a power level sufficient to heat at least a portion of the electron-emissive surface to an electron emitting temperature, from a laser source onto a cathode. The cathode generates an electron beam along a beam path by thermionic emission, and strikes a target positioned in its beam path. The target includes radiation emissive material that emits therapeutic radiation, such as x-rays, in response to incident accelerated electrons from the electron beam.

In a preferred embodiment, a substantially rigid housing encloses the thermionic cathode and the target. The housing defines a substantially evacuated interior region that extends along the beam path, between a proximal end and a distal end of the housing.

In one embodiment, the spiral-shaped thermionic cathode is made of a spiral-shaped conductive element. The spiral-shaped conductive element has a plurality of spaced apart turns, and defines an interstitial spacing between each successive turn of said conductive element. Because the spiral-shaped conductive element is enclosed within the substantially evacuated interior region, heat transfer across the interstitial spacing between each adjacent turn of the conductive element is essentially eliminated. By minimizing heat lost by thermal conduction, the efficiency of the miniaturized thermionic cathode is increased.

DETAILED DESCRIPTION

The present invention is directed to a miniaturized, low power therapeutic radiation source which includes an electron-beam activated therapeutic radiation source, and which uses a laser-heated thermionic cathode. As described in the PHLL-155 application, use of a thermionic cathode that is laser-heated significantly reduces the power requirements for such therapeutic radiation sources. The present invention features the use of a spiral-shaped thermionic cathode, which is configured so as to minimize energy lost from the incident laser radiation due to thermal conduction within the thermionic cathode. In this way, the power requirements for generating therapeutic radiation in such miniaturized radiation sources are further reduced.

Figure 1:
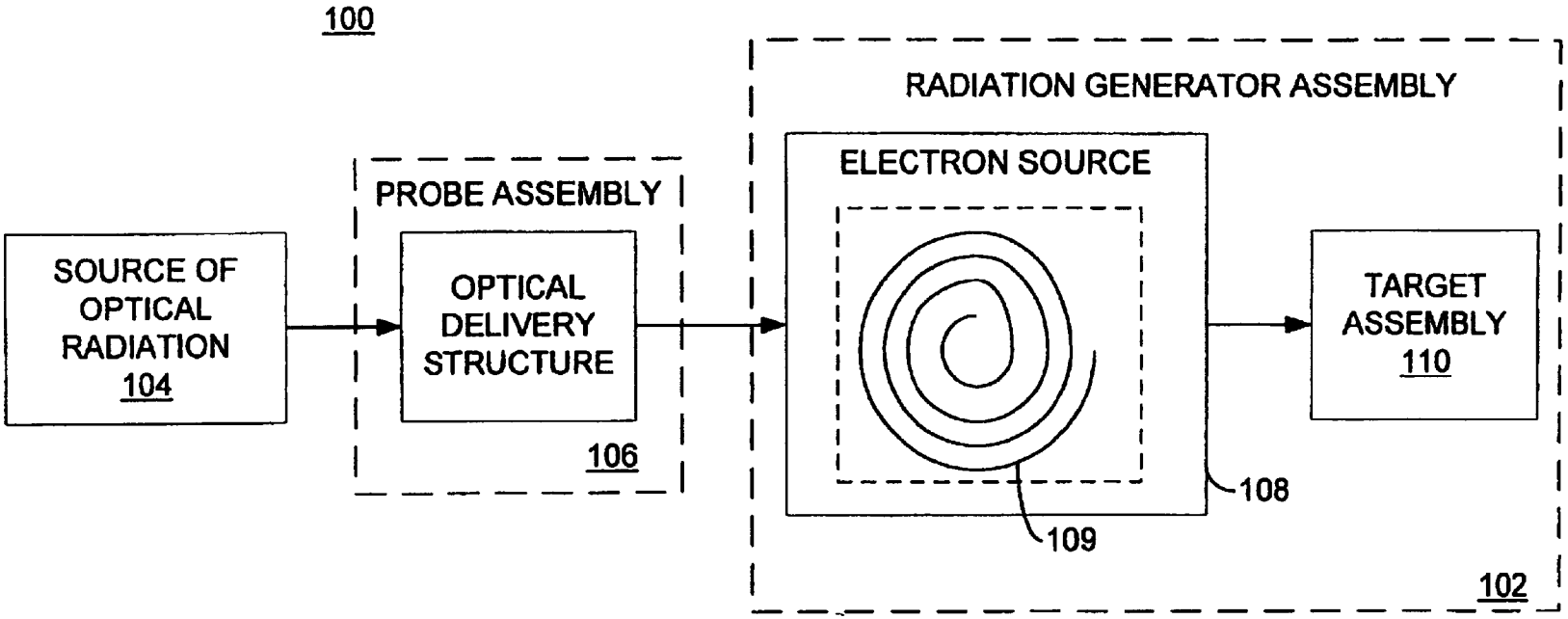
FIG. 1 is a schematic block diagram of an overview of one embodiment of a therapeutic radiation source constructed in accord with the present invention.

FIG. 1 is a schematic block diagram of an overview of one embodiment of a therapeutic radiation source 100, constructed according to the present invention, and including a spiral-shaped, laser-heated thermionic cathode. In overview, the system of the present invention includes a radiation generator assembly 102, a source of optical radiation 104, and a probe assembly 106. Preferably, the source of optical radiation 104 is a laser, so that the optical radiation generated by the source is substantially monochromatic, and coherent. The laser may be a diode laser, by way of example; however, other lasers known in the art may be used, such as a Nd:YAG laser, a Nd:$YVO_4$ laser, and a molecular laser.

The radiation generator assembly 102 includes an electron source 108, and a target assembly 110 that includes means for emitting therapeutic radiation in response to incident accelerated electrons from the electron beam. The electron source 108 includes a spiral-shaped thermionic cathode 109.

The probe assembly 106 includes optical delivery structure 112, such as a fiber optical cable assembly. The optical delivery structure 112 directs a beam of laser radiation generated by the laser 104 onto the electron source 108. The laser beam heats the thermionic cathode 109 in the electron source 108, so as to cause thermionic emission of electrons. In a preferred embodiment, the spiral-shaped thermionic cathode has a plurality of spaced apart turns, an interstitial spacing being defined between each successive turn. Heat loss in the cathode due to thermal conduction is minimized, due to the spiral-shaped configuration of the cathode.

Generally, the apparatus of the present invention operates at voltages in the range of approximately 10 keV to 90 keV, and electron beam currents in the range of approximately 1 nA to 100 μA. At those operating voltages and currents, radiation output is relatively low, and the apparatus may be made small enough to be adapted for implantation in medical therapeutic applications. In view of the low-level radiation output, adequate tissue penetration and cumulative dosage may be attained by positioning the radiation source adjacent to or within the region to be irradiated. Thus, therapeutic radiation is emitted from a well-defined, small source located within or adjacent to the region to be irradiated.

Figure 2A:
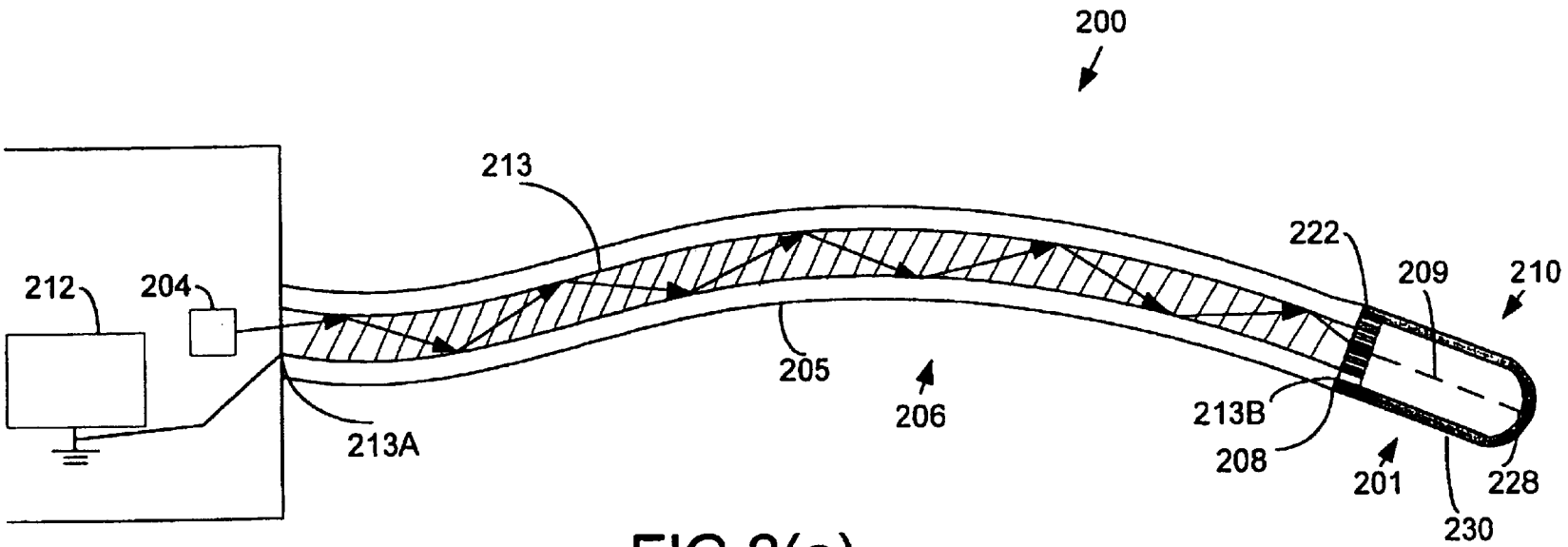
FIG. 2(a) is an overall, diagrammatic view of one embodiment of a therapeutic radiation source constructed according to the present invention.
Figure 2B:
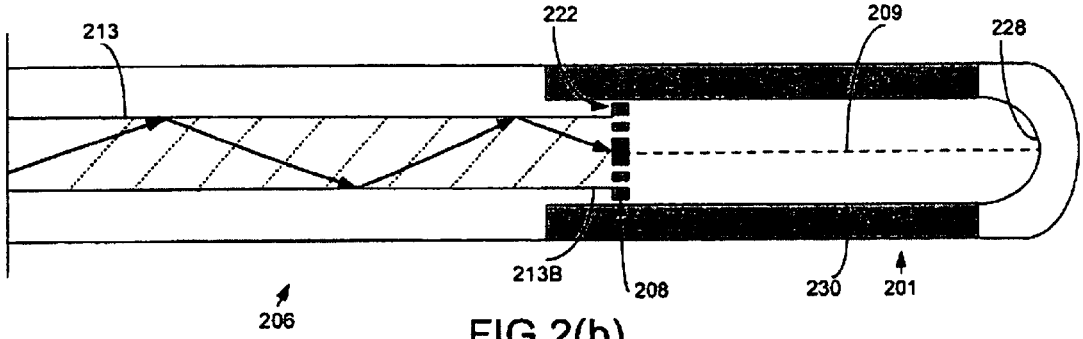
FIG. 2(b) provides an enlarged view of the radiation generator assembly, and the distal end of the probe assembly, constructed in accordance with the present invention.

FIGS. 2(a) and 2(b) show a diagrammatic view of one embodiment of the therapeutic radiation source apparatus 200 constructed according to the present invention. In the embodiment illustrated in FIG. 2(a), the apparatus 200 includes a laser source 204, a probe assembly 206, and a radiation generator assembly 201. The radiation generator assembly 201 includes an electron source 208 that generates an electron beam along a beam path 209, and a target assembly 210 positioned in the beam path. In the illustrated embodiment, a high voltage power supply 212 is also provided. The probe assembly 206 couples both the laser source 204 and the high voltage power supply 212 to the target assembly 210. FIG. 2(a) provides an overall view of the therapeutic radiation source 200, whereas FIG. 2(b) provides an enlarged view of 1) the radiation generator assembly 201, and 2) the distal end of the probe assembly 206.

Referring to both FIGS. 2(a) and 2(b), the electron source 208 includes a thermionic cathode 222 having an electron emissive surface. The thermionic cathode 222 is spiral-shaped, and includes a spiral-shaped conductive element having a plurality of spaced apart turns that define an interstitial spacing between adjacent turns. The conductive element may be a wire, by way of example. The conductive element may also be a photochemically machined flat spiral of cathode material. The spiral arrangement of the wire results in a reduction of conductive heat loss in the cathode.

The electron source 208 also includes means for establishing an accelerating electric field. In one embodiment, the means for establishing an accelerating electric field may be the high voltage power supply 212. The high voltage power supply 212 may establish an acceleration potential difference between the thermionic cathode 222 and the grounded target element 228, so that electrons emitted from the thermionic cathode 222 are accelerated toward the target element 228, and an electron beam is generated. The electron beam is preferably thin (e.g. 1 mm or less in diameter), and is established along a beam path 209 along a nominally straight reference axis that extends to the target assembly 210. The target assembly 210 is positioned in the beam path 209. The distance from the electron source 208 to the target assembly 210 is preferably less than 2 mm.

The high voltage power supply 212 preferably satisfies three criteria: 1) small in size; 2) high efficiency, so as to enable the use of battery power; and 3) independently variable x-ray tube voltage and current, so as to enable the unit to be programmed for specific applications. Preferably, the power supply 212 includes selectively operable control means, including means for selectively controlling the amplitude of the output voltage and the amplitude of the beam generator current. A high-frequency, switch-mode power converter can be used to meet these requirements. The most appropriate topology for generating low power and high voltage is a resonant voltage converter working in conjunction with a high voltage, Cockroft-Walton-type multiplier. Low-power dissipation, switch-mode power-supply controller-integrated circuits (IC) are currently available for controlling such topologies with few ancillary components. A more detailed description of the power supply 212 is provided in U.S. Pat. Nos. 5,153,900 and 5,428,658.

The target assembly 210 preferably includes a target element 228 spaced apart from and opposite the electron emissive surface of the thermionic cathode 222, where the target element 228 has at least one radiation emissive element adapted to emit therapeutic radiation in response to incident accelerated electrons from the electron emissive surface of the thermionic cathode 222. In a preferred embodiment, the emitted therapeutic radiation consist of x-rays, however it should be noted that the scope of this invention is not limited to x-rays, and other forms of therapeutic radiation may also be generated.

In one embodiment, the target element 228 is a small beryllium (Be) window, coated on the side exposed to the incident electron beam with a thin film or layer of a high-Z, x-ray emissive element, such as tungsten (W), uranium (U) or gold (Au). By way of example, when the electrons are accelerated to 30 keV−, a 2 micron thick gold layer absorbs substantially all of the incident electrons, while transmitting approximately 95% of any 30 keV−, 88% of any 20 keV−, and 83% of any 10 keV−x-rays generated in that layer. In this embodiment, the beryllium target element 228 is 0.5 mm thick. With this configuration, 95% of the x-rays generated in directions normal to and toward the target element 228, and having passed through the gold layer, are then transmitted through the beryllium window and outward at the distal end of the probe assembly 206.

In some forms of the invention, the target element 228 may include a multiple layer film, where the differing layers may have different emission characteristics. By way of example, the first layer may have an emission versus energy peak at a relatively low energy, and the second underlying layer may have an emission versus energy peak at a relatively high energy. With this form of the invention, a low energy electron beam may be used to generate x-rays in the first layer, to achieve a first radiation characteristic, and high energy electrons may be used to penetrate through to the underlying layer, to achieve a second radiation characteristic.

In this embodiment, x-rays can be generated in the target assembly in accordance with pre-selected beam voltage, current, and target element composition. The generated x-rays pass through the beryllium target substrate with minimized loss in energy. As an alternative to beryllium, the target substrate may be made of carbon, ceramic such as boron nitride, or other suitable material which permits x-rays to pass with a minimum loss of energy. An optimal material for target substrate is carbon in its diamond form, since that material is an excellent heat conductor. Using these parameters, the resultant x-rays have sufficient energy to penetrate into soft tissues to a depth of a centimeter or more, the exact depth dependent upon the x-ray energy distribution.

In another embodiment of the invention, the target may be a solid, high-Z material, with x-rays being emitted in an annular beam perpendicular to the tube axis.

The radiation generator assembly 201, which can be for example 1 to 2 cm-in length, extends from the end of the probe assembly 206 and includes a capsule 230 which encloses the target assembly. According to one embodiment, the radiation generator assembly 201 is rigid in nature and generally cylindrical in shape. In this embodiment the cylindrical capsule 230 enclosing the radiation generator assembly 201 can be considered to provide a substantially rigid housing 230 for the electron source 208. In one embodiment, the electron source 208 and the target assembly 210 is disposed within the capsule 230, with the thermionic cathode disposed at an input end of the capsule 230, and the target assembly 210 disposed at an output end of the housing 230. The capsule 230 defines a substantially evacuated interior region extending along the beam axis 209, between the thermionic cathode 222 at the input end of the capsule 230 and the target assembly 210 at the output end of the housing 230. The inner surface of the radiation generator assembly 201 is lined with an electrical insulator, or a semiconductor, while the external surface of the assembly is electrically conductive. According to a preferred embodiment, the radiation generator assembly 201 is hermetically sealed to the end of the probe assembly, and evacuated. According to another embodiment, the entire probe assembly 206 is evacuated.

The probe assembly 206 couples the laser source 204 and the high voltage power supply 212 to the target assembly 210. In the illustrated embodiment, the probe assembly 206 includes a flexible, electrically conductive catheter 205 extending along a probe axis between a proximal end and a distal end of the catheter 205. The probe assembly 206 includes optical delivery structure 213 having an originating end 213A and a terminating end 213B. The terminating end 213B of the optical delivery structure 213 is affixed to the radiation generator assembly 201.

In a preferred embodiment, the optical delivery structure 213 is a flexible fiber optical cable. In this embodiment, the flexible catheter 205 that encloses the fiber optical cable 202 is a small-diameter, flexible, metallic outer tube. In this embodiment, the target assembly 210 includes an electrically conductive outer surface. Preferably, both the metallic tube 205 and the target element 228 are set at ground potential, in order to reduce the shock hazard of the device. In one embodiment, the fiber optical cable has a diameter of about 200 microns, and the flexible metallic tube 205 has a diameter of about 1.4 mm.

In a preferred embodiment, the fiber optic cable 213 includes an electrically conductive outer surface. For example, the outer surface of the fiber optic cable 213 may be made conductive by applying an electrically conductive coating. The electrically conductive outer surface of the fiber optic cable 213 provides a connection to the thermionic cathode 222 from the high voltage power supply 212. In this embodiment, the radiation generator assembly 201 also has an electrically conductive outer surface. Preferably, both the flexible metallic sheath 205 and the outer conductive surface of the radiation generator assembly 201 are set at ground potential, in order to reduce the shock hazard of the device. The flexible sheath 205 couples a ground return from the target element 228 to the high voltage power supply 212, thereby establishing a high voltage field between the thermionic cathode 222 and the target element 228. In an exemplary embodiment, the fiber optic cable 213 may have a diameter of about 200 microns, and the flexible metallic sheath 205 may have a diameter of about 1.4 mm. A layer of dielectric material provides insulation between the outer surface of the fiber optic cable 213 and the inner surface of the metallic sheath 205.

Getters may be positioned within the housing.230. The getters aid in creating and maintaining a vacuum condition of high quality. The getter has an activation temperature, after which it will react with stray gas molecules in the vacuum. It is desirable that the getter used have an activation temperature that is not so high that the x-ray device will be damaged when heated to the activation temperature.

The thermionic cathode 222 has an electron emissive surface, and is typically formed of a metallic material. Suitable metallic materials forming the cathode 222 may include tungsten, thoriated tungsten, other tungsten alloys, thoriated rhenium, and tantalum. In one embodiment, the cathode 222 may be formed by depositing a layer of electron emissive material on a base material, so that an electron emissive surface is formed thereon. By way of example, the base material may be formed from one or more metallic materials, including but not limited to Group VI metals such as tungsten, and Group II metals such as barium. In one form, the layer of electron emissive material may be formed from materials including, but not limited to, aluminum tungstate and scandium tungstate. The thermionic cathode 222 may also be an oxide coated cathode, where a coating-of the mixed oxides of barium and strontrium, by way of example, may be applied to a metallic base, such as nickel or a nickel alloy. The metallic base may be made of other materials, including Group VI metals such as tungsten.

The thermionic cathode is spiral-shaped, configured to minimize heat loss through thermal conduction. For a disc-shaped or planar tungsten thermionic cathode, the percentage of incident radiation that is absorbed at an incident spot on the cathode is typically about 40%. Of the 40% absorbed, however, further losses are caused because of thermal conduction within the cathode. In the present invention, the use of a spiral-shaped cathode is disclosed, wherein heat loss through thermal conduction is minimized, because the cathode is in the shape of a spiral coil having a plurality of spaced apart turns. Heat loss through thermal conduction is substantially reduced, as compared to heat conduction within a disk-shaped thermionic cathode, because no heat transfer occurs across the vacuum between adjacent, spaced apart turns of the conductive element forming the cathode.

The fiber optical cable 202 is adapted to transmit laser radiation, generated by the laser source 204 (shown in FIG. 2(a)) and incident on the originating end of the fiber optical cable assembly, to the terminating end of the fiber optical cable assembly 213. The fiber optical cable 202 is also adapted to deliver a beam of the transmitted laser radiation to impinge upon the electron-emissive surface of the thermionic cathode 222. The beam of laser radiation must have a power level sufficient to heat at least a portion of the electron-emissive surface to an electron emitting temperature so as to cause thermionic emission of electrons from the surface.

In operation, the laser beam shining down the fiber optic cable 213 impinges upon the surface of the thermionic cathode 222, and rapidly heats the surface to an electron emitting temperature, below the melting point of the metallic cathode 222. Upon reaching of the surface of a electron emitting temperature, electrons are thermionically emitted from the surface. The high voltage field between the cathode 222 and the target element 228 (shown in FIGS. 3 and 4) accelerates these electrons, thereby forcing them to strike the surface of the target element 228 and produce x-rays. In one embodiment of the invention, a Nd:YAG laser was coupled into a SiO2 optical fiber having a diameter of 400 microns. A 20 kV power supply was used, and a thermionic cathode made of tungsten was used. Even with a disc-shaped, planar cathode, only a few watts of power was needed to generate over 100 μA of electron current. In another example, an infrared diode laser was used in conjunction with a spiral-shaped, half millimeter etched cathode, to achieve about 100 μA of electron current with only 180 mW of power, thereby substantially reducing the power requirements for the apparatus 200.

Figure 3A:
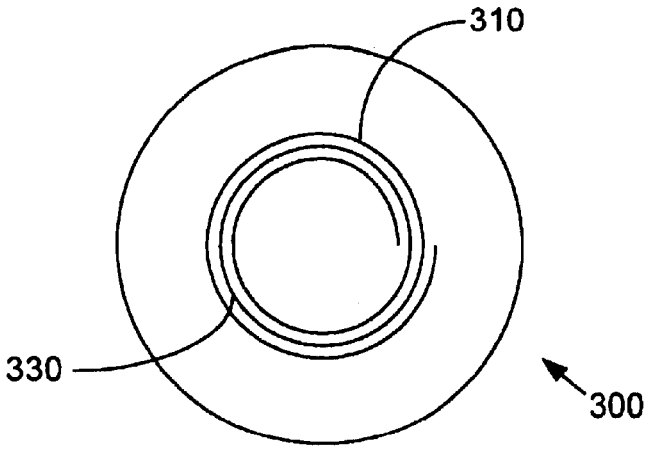
FIG. 3(a) shows a plane view spiral-shaped thermionic cathode, constructed in accordance with the present invention.
Figure 3B:
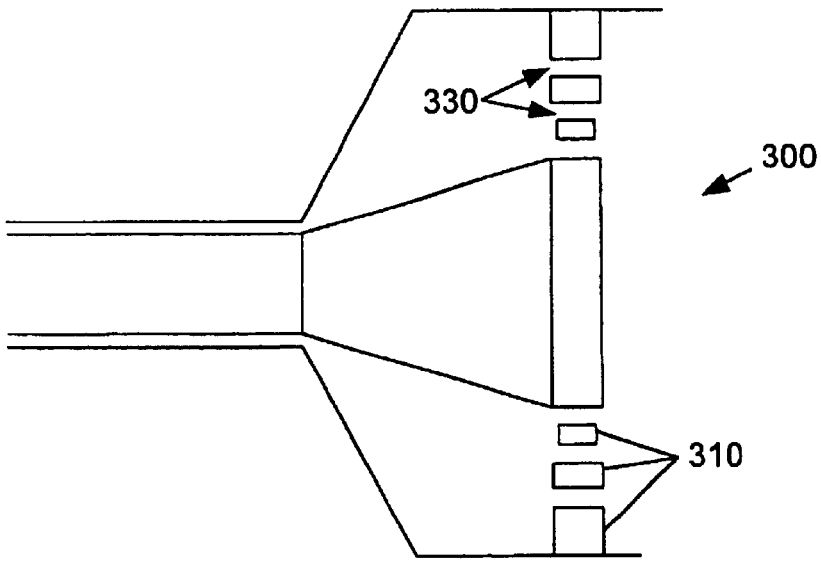
FIG. 3(b) shows a side view of a spiral-shaped thermionic cathode, constructed in accordance with the present invention.

FIGS. 3(a) and 3(b) illustrate in more detail a spiral-shaped cathode 300 constructed in accordance with the present invention. FIG. 3(a) illustrates a planar view of the spiral-shaped cathode 300, whereas FIG. 3(b) illustrates a side view. In a preferred embodiment, the spiral-shaped cathode 300 may be fabricated by using photoetching techniques known in the art. The spiral-shaped cathode 300 includes a conductive element 310 arranged in a spiral shape. The material forming the spiral-shaped conductive element is preferably a high melting point metal adapted to withstand high temperature uses. Suitable materials forming the cathode may include tungsten, thoriated tungsten, other tungsten alloys, tantalum, rhenium, thoriated rhenium, and molybdenum. Preferably, the spiral-shaped conductive element 310 forms a planar coil, although other forms of conductive coils may be used, such as helical coils. Spiral coils of various shapes can be used. For example, each of the plurality of spaced apart turns may have a substantially circular shape, when viewed from the longitudinal direction. Alternatively, the spiral coil may have other transverse sectional shapes, such as oval, square, or rectangular.

The spiral-shaped conductive element 310 has a plurality of spaced apart turns, which define an interstitial spacing 330 between each successive turn. The conductive element 310 may have a length of about 2 mm to about 7 mm, although other dimensions are also within the scope of this invention. The distance between adjacent turns of the conductive element 310 may be about 25 microns to about 50 microns, although other dimensions are also within the scope of this invention. Since the spiral-shaped cathode 300 is disposed within the vacuum within the capsule 230 (shown in FIGS. 2(a) and 2(b)), heat transfer across the interstitial spacing 330 between adjacent turns of the conductive element 310 is essentially eliminated. In this way, heat loss in the thermionic cathode 300 that is caused by thermal conduction is substantially reduced.

In an exemplary embodiment, the spiral-shaped thermionic cathode 300 was fabricated using a conductive wire 0.002 mm thick, and 7.4 mm long. In this embodiment, the conductive wire defined two spaced-apart turns. The power loss caused by thermal conduction was only 0.126 Watts, as compared to planar, disk-shaped cathodes, in which the power loss due to thermal conduction was about 1.1 Watts. The power loss caused by thermal radiation was about 140 mW.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A therapeutic radiation source, comprising:

A. a radiation generator assembly, comprising:

a. an electron source for emitting electrons to generate an electron beam along a beam path, said electron source including a thermionic cathode having an electron emissive surface, and b. a target positioned in said beam path, said target including means for emitting therapeutic radiation in response to incident accelerated electrons from said electron beam; wherein said thermionic cathode comprises a spiral-shaped conductive element;

B. a source of optical radiation; and

C. optical delivery structure having an originating end and a terminating end and adapted for transmitting to said terminating end optical radiation generated by said source and incident on said originating end; and wherein said optical delivery structure are adapted for directing a beam of said transmitted optical radiation upon a surface of said thermionic cathode; and wherein said beam of optical radiation has a power level sufficient to heat at least a portion of said surface to an electron emitting temperature so as to cause thermionic emission of electrons from said surface.

2. A therapeutic radiation source according to claim 1, further comprising:

a substantially rigid housing enclosing said thermionic cathode and said target, wherein said housing defines a substantially evacuated interior region extending along said beam path between a proximal end and a distal end of said housing.

3. A therapeutic radiation source according to claim 1, wherein said thermionic cathode is disposed at said input end of said housing.

4. A therapeutic radiation source according to claim 1, further comprising a radiation transmissive window at an output end of said housing, wherein therapeutic radiation emitted from said target is directed through said radiation transmissive window.

5. A therapeutic radiation source according to claim 1, wherein said spiral-shaped conductive element defines a plurality of spaced apart turns.

6. A therapeutic radiation source according to claim 5, wherein said conductive element defines an interstitial space between each successive turn.

7. A therapeutic radiation source according to claim 5, wherein said spiral-shaped conductive element forms a planar coil.

8. A therapeutic radiation source according to claim 5, wherein said spiral-shaped conductive element forms a helical coil.

9. A therapeutic radiation source according to claim 5, wherein the distance between adjacent turns of said [conductive coil] *spiral-shaped conductive element* is from about 25 microns to about 50 microns.

10. A therapeutic radiation source according to claim 5, wherein each of said plurality of spaced apart turns has a transverse sectional shape that is substantially circular.

11. A therapeutic radiation source according to claim 1, wherein said optical delivery structure comprises a fiber optical cable.

12. A therapeutic radiation source according to claim 1, wherein said fiber optical cable has a diameter between about 100 microns to about 200 microns.

13. A therapeutic radiation source according to claim 5, wherein said spiral-shaped conductive [coil] *element* has a length between about 2 mm to about 7 mm.

14. A therapeutic radiation source according to claim 1, wherein the power required for heating said electron emissive surface of said cathode so as to generate an electron beam forming a current of about 2 micro amps is between about 0.1 Watt to about 1.0 Watt.

15. A therapeutic radiation source according to claim 1, wherein said optical source is a laser, and wherein said beam of optical radiation is substantially monochromatic and coherent.

16. A therapeutic radiation source according to claim 1, wherein said therapeutic radiation comprises x-rays.

17. A therapeutic radiation source according to claim 1, wherein power loss caused by thermal conduction is less than 0.2 Watts.

18. A therapeutic radiation source according to claim 17, wherein heat transfer across the spacing between each adjacent turn of said conductive element is essentially eliminated, thereby substantially reducing in said thermionic cathode heat loss caused by thermal conduction.

19. A therapeutic radiation source according to claim 1, further including means for establishing an accelerating electric field which acts to accelerate electrons emitted from said electron source toward said target.

20. A therapeutic radiation source according to claim 19, wherein said means for establishing an accelerating electric field is a power supply.

21. A therapeutic radiation source, comprising:

A. a radiation generator assembly, comprising:

a. an electron source for emitting electrons to generate an electron beam along a beam path, said electron source including a thermionic cathode having an electron emissive surface, and b. a target positioned in said beam path, said target including means for emitting therapeutic radiation in response to incident accelerated electrons from said electron beam; and c. a substantially rigid housing enclosing said thermionic cathode and said target, wherein said housing defines a substantially evacuated interior region extending along said beam path between an input end and an output end of said housing.

B. a source of optical radiation; and

C. optical delivery structure having an originating end and a terminating end and adapted for transmitting to said terminating end optical radiation generated by said source and incident on said originating end, said optical delivery structure being adapted for directing a beam of said transmitted optical radiation upon a surface of said thermionic cathode, wherein said beam of optical radiation has a power level sufficient to heat at least a portion of said surface to an electron emitting temperature so as to cause thermionic emission of electrons from said surface; and wherein said thermionic cathode comprises a spiral-shaped conductive element having a plurality of spaced apart turns.

*22. A probe having a radiation source at a distal end, comprising:*

*A. a probe assembly including an optical delivery structure adapted for transmitting optical radiation;*

*B. an optical source for generating optical radiation directed to an end of said optical delivery structure;*

*C. a radiation source coupled to a distal end of said optical delivery structure, said radiation source comprising a thermionic cathode and a target element;*

*a. wherein the thermionic cathode is responsive to said optical radiation transmitted to said distal end to emit electrons, and wherein said thermionic cathode comprises a spiral-shaped conductive element; and*

*b. wherein said target element is responsive to incident electrons emitted from said thermionic cathode to emit radiation;*

*D. means for establishing an accelerating electric field extending between said electron source toward said target element, the electric field being effective to accelerate electrons emitted from the thermionic cathode toward said target element;*

*Wherein said optical delivery structure is adapted to direct a beam of optical radiation transmitted therethrough to impinge upon a surface of the thermionic cathode, and wherein said beam of transmitted optical radiation has a power level sufficient to heat at least a portion of said surface to an electron emitting temperature so as to cause thermionic emission of electrons from said surface.*

*23. A probe in accordance with claim 22, wherein said optical source comprises a laser.*

*24. A probe in accordance with claim 22, wherein said radiation source comprises an x-ray source, and said radiation emitted from said target element comprises x-rays.*

*25. A probe in accordance with claim 22, wherein said optical delivery structure comprises a fiber optic cable.*

*26. A probe in accordance with claim 22, wherein said radiation source comprises a substantially rigid housing enclosing said thermionic cathode and said target element, wherein said housing defines a substantially evacuated interior region extending along said beam path between a proximal end and a distal end of said housing.*

*27. A probe in accordance with claim 22, wherein said spiral-shaped conductive element defines a plurality of spaced apart turns with an interstitial space between each successive turn.*

*28. A probe in accordance with claim 22, wherein said spiral-shaped conductive element forms one of a planar coil and a helical coil.*

*29. A radiation source, comprising:*

*A. a probe assembly including an optical delivery structure, said optical delivery structure being adapted for transmitting optical radiation incident on a proximal end thereof to a distal end thereof;*

*B. an optical source for generating a beam of optical radiation directed to said proximal end of said optical delivery structure;*

*C. a radiation generator assembly coupled to said probe assembly, including:*

*a. an electron source, responsive to optical radiation transmitted to said distal end of said optical delivery structure, for emitting electrons, the electron source including a thermionic cathode having an electron emissive surface; wherein said*

*b. a target element including at least one radiation emissive material adapted to emit radiation in response to incident accelerated electrons from said electron source; and*

*D. means for providing an accelerating voltage between said electron source and said target element so as to establish an accelerating electric field which acts to accelerate electrons emitted from said electron source toward said target element;*

*wherein said optical delivery structured is adapted for directing a beam of optical radiation transmitted therethrough to impinge upon a surface of said thermionic cathode, and wherein said beam of transmitted optical radiation has a power level sufficient to heat at least a portion of said surface to an electron emitting temperature so as to cause thermionic emission of electrons from said surface.*

*30. A flexible probe having an x-ray tube as a distal end, comprising:*

*A. an optical source for generating optical radiation,*

*B. a flexible optical fiber having a proximal end and a distal end, and adapted fro transmitting optical radiation incident on said proximal end to said distal end;*

*C. an x-ray tube coupled to a distal end of said optical fiber, comprising a substantially rigid housing enclosing a thermionic cathode and an x-ray target,*

*a. wherein the thermionic cathode is responsive to said optical radiation transmitted to said distal end to emit electrons; wherein said thermionic cathode comprises a spiral-shaped conductive element; and*

*b. wherein said x-ray target is responsive to incident electrons emitted from said thermionic cathode to emit x-rays;*

*D. means for establishing an electric field to accelerate electrons emitted from the thermionic cathode toward said x-ray target;*

*wherein said optical fiber is adapted to direct a beam of optical radiation transmitted therethrough to impinge upon a surface of the thermionic cathode, and wherein said beam of transmitted optical radiation has a power level sufficient to heat at least a portion of said surface to an electron emitting temperature so as to cause thermionic emission of electrons from said surface.*

* * * * *

UNITED STATES PATENT AND TRADEMARK OFFICE

CERTIFICATE OF CORRECTION

PATENT NO. : RE41,741 E
APPLICATION NO. : 10/790636
DATED : September 21, 2010
INVENTOR(S) : Mark Dinsmore It is certified that error appears in the above-identified patent and that said Letters Patent is hereby corrected as shown below:

Title page item (54) replace the title with --OPTICALLY DRIVEN THERAPEUTIC RADIATION SOURCE HAVING A SPIRAL-SHAPED THERMIONIC CATHODE--

In column 1, lines 1-3, replace the title --OPTICALLY DRIVEN THERAPEUTIC RADIATION SOURCE HAVING A SPIRAL-SHAPED THERMIONIC CATHODE--

In column 3, line insert the following text after "Ser. No." --09/884,561--

Signed and Sealed this
Twenty-fifth Day of January, 2011

David J. Kappos

David J. Kappos
*Director of the United States Patent and Trademark Office*